United States Patent [19]

Walker

[11] Patent Number: 5,114,684

[45] Date of Patent: May 19, 1992

[54] IN-LINE ELECTROMAGNETIC ENERGY WAVE APPLICATOR

[75] Inventor: David R. Walker, Clearwater, Fla.

[73] Assignee: SeraWaste Systems Corporation, Tampa, Fla.

[21] Appl. No.: 625,666

[22] Filed: Dec. 13, 1990

[51] Int. Cl.⁵ .............................................. B01J 19/08
[52] U.S. Cl. ................................ 422/186; 204/180.6; 422/186.04; 422/186.3
[58] Field of Search .............. 422/186, 186.04, 186.05; 34/1, 4, 136; 432/106

[56] References Cited

U.S. PATENT DOCUMENTS

| | | | |
|---|---|---|---|
| Re. 29,590 | 3/1978 | Whelan | 250/493 |
| 919,445 | 4/1909 | Zohman | 422/186.19 |
| 3,488,858 | 1/1970 | Bilbrough | 34/1 |
| 3,491,457 | 1/1970 | Schreiber et al. | 34/1 |
| 3,829,982 | 8/1974 | Pray et al. | 34/4 |
| 3,967,385 | 7/1976 | Culbertson | 34/4 |
| 4,087,921 | 5/1978 | Blok | 34/1 |
| 4,189,363 | 2/1980 | Beitzel | 204/157.1 R |
| 4,193,448 | 3/1980 | Jeambey | 166/248 |
| 4,330,946 | 5/1982 | Courneys | 34/1 |
| 4,410,553 | 10/1983 | McGinty | 426/243 |
| 4,565,670 | 1/1986 | Miyazaki et al. | 422/186.04 |
| 4,608,261 | 8/1986 | MacKenzie | 426/242 |

Primary Examiner—Brooks H. Hunt
Assistant Examiner—Daniel J. Jenkins
Attorney, Agent, or Firm—Foley & Lardner

[57] ABSTRACT

An in-line microwave applicator has an electromagnetic energy wave generating unit which transmits waves, particularly microwaves, dispersing from a longitudinal axis. The dispersing waves are interrupted by microwave diverters which cause the wave lengths to be transmitted through holes from the first chamber to a second surrounding chamber. The second surrounding chamber has interior walls which are reflective to the microwaves and may have a spiral rib to enhance reflectivity. Product for heating is passed through the second chamber to be irradiated by microwaves exiting the holes from the first chamber. The holes are generally elongate in shape and can be surrounded with microwave transparent material to prevent material from falling through. The microwave diverters can be protrusions extending from the holes into the inner chamber by increasing amounts as the distance from the microwave energy generating unit increases. Alternatively, cones placed at varying angles, a generally spiral shape member, or a series of disks can be used as microwave diverters. Product can be carried through the second chamber using a single or variable pitch helix or screw.

74 Claims, 8 Drawing Sheets

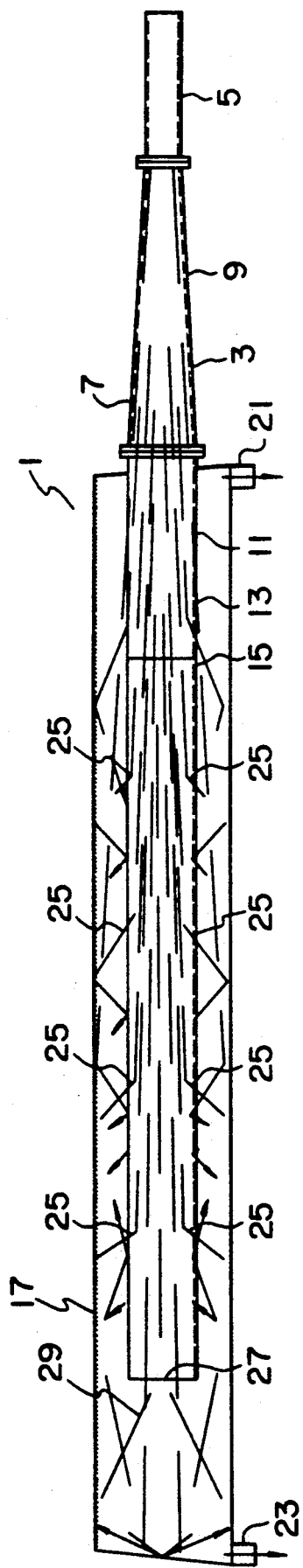
FIG.1
FIG.2

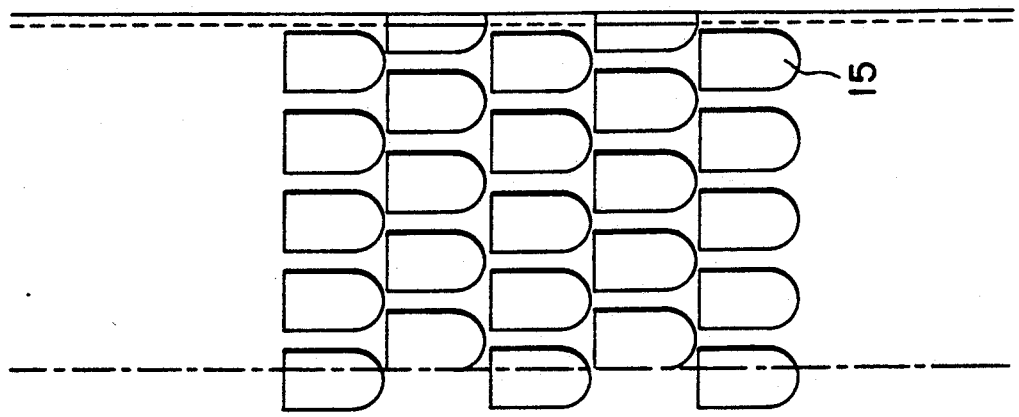
FIG. 12
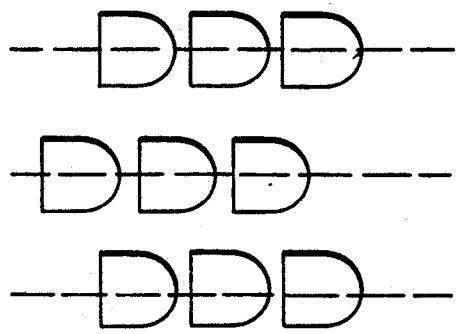
FIG. 3
SLOTTED HOLE PUNCH PATTERN

STRAIGHT SHAFT STERILIZER

COMPRESSION SHAFT STERILIZER

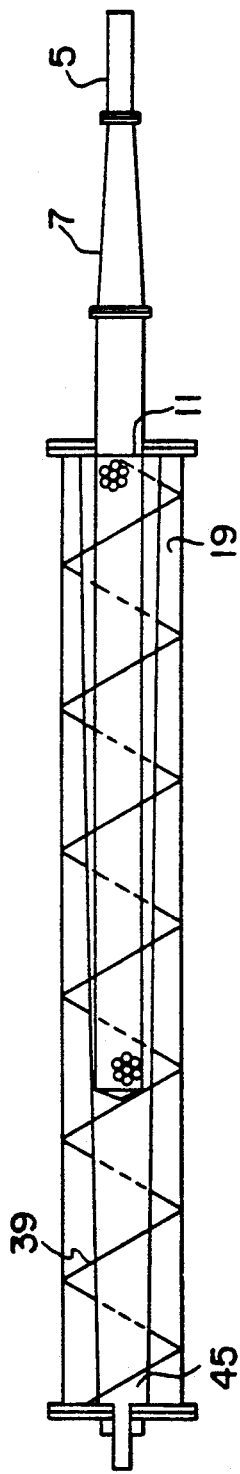
FIG. 6 DECOMPRESSION SHAFT STERILIZER
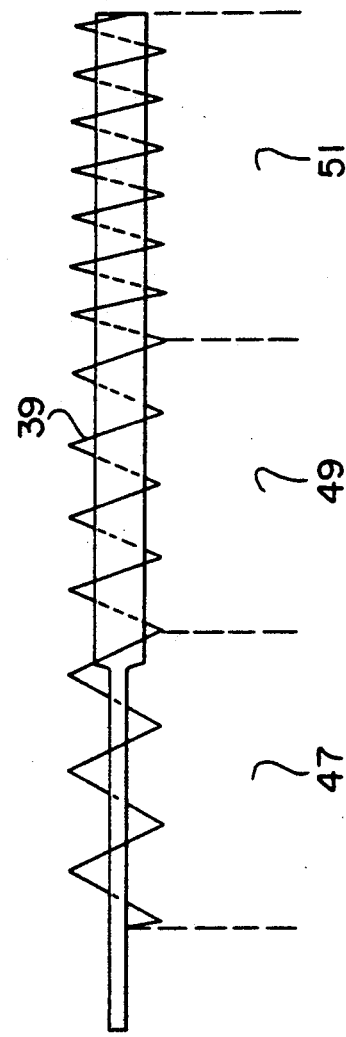
FIG. 7 VARIABLE PITCH SCREW

IN-LINE ELECTROMAGNETIC ENERGY WAVE APPLICATOR

BACKGROUND OF THE INVENTION

The present invention relates to apparatus and methodology for applying electromagnetic wave energy, particularly microwaves, to a product to be heated, such as contaminated and infectious waste products to be sterilized.

Environmental concerns have motivated a search for waste incineration systems which efficiently incinerate waste materials while decreasing pollutant emissions. The need for such systems is particularly critical for disposal of contaminated and infectious wastes, such as hospital waste. Traditional incineration systems burn waste at relatively low temperatures and tend to emit unacceptably high levels of fly ash and other pollutants.

The use of electromagnetic energy waves, in particular microwaves, to heat materials is well known. One heating apparatus using microwaves is disclosed in U.S. Pat. No. 4,565,670 to Miyazaki. Miyazaki discloses a stationary outer cylinder and a rotatable inner cylinder to form a passage in between the cylinders for the continuous heat treatment of a substance passing through the passage. Material passes from inlet pipe 1 through passage 14 to outlet pipe 2. As the material traverses the path it is exposed to microwaves through waveguides 3 located at the inlet end position, the outlet end position and an intermediate position on the circumferential wall of the outer cylinder 4. By applying microwave radiation from the periphery, Miyazaki requires the application microwaves at multiple locations.

U.S. Pat. No. 4,608,261 to MacKenzie discloses a method and apparatus for producing a puffed foodstuff using a microwave generator 19 mounted within a microwave cavity 16 to apply microwave energy to raw material passing through a tubular conveyance section 17. Like Miyazaki, MacKenzie situates the microwave generator at a point above the material to be radiated.

U.S. Pat. No. 4,330,946 to Courneya discloses a high efficiency material drying apparatus with microwave sources 30 located above a primary chamber 40, where the heat is concentrated on the material moved along an auger pathway. Microwave sources or magnetrons 30 are offset to direct their energy to the location of the majority of material at any instant. Thus, Courneya also has the disadvantage of requiring a plurality of points applying microwaves to the material being heated.

U.S. Pat. No. 4,087,921 discloses a microwave drying apparatus with microwave units 17 located on opposite sides of drum 11 which has longitudinally extending buffers 43 projecting radially inward from the inner surface of the drum. This causes a tumbling action of material passing through the drum to enhance the drying effect produced by the microwave units 17. Again a plurality of microwave application locations is required.

All of the patent documents discussed above require the application of microwaves using one or more microwave sources located at various locations surrounding the material to be heated. As a result, each of the units is costly and inefficient.

U.S. Pat. No. 4,193,448 to Jeambey discloses an apparatus for recovery of petroleum from petroleum impregnated media. The apparatus uses a microwave generator and a guide for directing microwaves to a dispersing chamber for heating the media. A plurality of holes is used for the flow of heated petroleum into the petroleum chamber. In operation, a hole is drilled in a petroleum impregnated media such as rock or shale and the apparatus is inserted into the hole. A drive motor is energized to rotate blades 50 of mixing device 48 causing microwaves to be dispersed from dispersing chamber 28 through the microwave transparent shell portion 46 into the surrounding media. The media is thus heated and the heated petroleum drains into the drilled hole. Shell 16 is moved up and down to facilitate recovery of oil into the chamber 32 through holes 64. Microwaves do not pass through the holes.

U.S. Pat. No. 4,410,553 to McGinty discloses a method and apparatus for cooking particular foodstuffs. The apparatus uses an elongated source of radiant heat, preferably a single resistance electric heater element which emits infrared radiation. Alternatively, multiple bar resistance electric heater elements having an associated concave reflector could be used. McGinty also discloses the use of a helix which can rotate to advance foodstuffs or can be fixed inside a retaining means and rotate therewith. The helix is further disclosed to have a variable pitch with the smallest pitch being in the area where the cooking is conducted for the longest length of time. Neither Jeambey nor McGinty discloses the use of reflected microwaves to provide heating of a material passing from an inlet to an outlet. In addition, none of the references discloses an efficient means for using a single source of microwave radiation to heat a product. Thus, the current art fails to disclose an in-line microwave applicator which can apply microwaves to material to be heated in an efficient manner.

SUMMARY OF THE INVENTION

It is therefore an object of the present invention to provide a less costly and more efficient system for applying electromagnetic energy to material to be heated.

It is still another object of the invention to provide substantially uniform heating of material without hot spots to extremely high temperatures, where necessary.

It is another object of the invention to provide an efficient in-line microwave applicator which requires only a single source of microwave energy to heat a product to high levels, for example, to sterilize infectious wastes.

It is another object of the invention to eliminate the need for multiple radiation sources around a periphery of material to be heated.

It is a further object of the invention to improve heating efficiency by making use of direct and reflected energy in heating product.

It is a further object of the invention to divert microwave energy from a single microwave energy source to heat a product moving along an axis parallel to a longitudinal axis of the microwave source.

It is a further object of the invention to divert such microwaves through holes in the walls of a first chamber into which the microwaves are applied while the product to be heated is passed through a second chamber surrounding the first chamber.

It is a further object of the invention to divert the microwaves in the first chamber to the holes using protrusions extending from the holes, with the protrusions progressively increasing in size as the microwaves travel farther from the source of microwave generation.

It is still another object of the invention to divert microwaves through the holes using either diverting discs or a spiral shaped member which interrupts the microwaves travelling in the first chamber.

It is still another object of the invention to configure an outer chamber surrounding an inner chamber having holes through which the microwaves pass to accommodate products of various thickness and moisture contents.

It is still another object of the invention to cover the holes of the first chamber with one or more sleeves of substantially microwave transparent material, such as TEFLON, to prevent waste product from being communicated into the first chamber.

It is still another object of the invention to provide a conveying means for non-liquid products to be heated in the outer chamber.

It is still another object of the invention to configure the conveying means to accommodate products of various thicknesses and moisture content.

It is still another object of the invention to provide a helical or screw type conveying means having a straight shaft and full pitch for products which have a consistent moisture mix to permit maximum loading of the unit with the variation of sterilization controlled only by the speed of the helix rotation.

It is another object of the invention to provide a straight shaft with variable pitch for use with products with higher moisture content by restricting the in-feed flow area and the length of the wave exposure to the depth of material.

It is still a further object of the invention that the variation of the pitch along the length of the helix slow the product flow and increase the holding time in the core to increase the efficiency of microwave exposure.

It is another object of the invention to provide a compression shaft sterilizer in the outer chamber in which the exposure to the microwave pattern is maximized on a discharge end by decreasing the product bed depth.

It is a still further object of the invention to vary the pitch on the compressive microwave sterilizer shaft to slow or speed up the transfer of material through the system resulting in an increase or decrease in microwave exposure.

It is another object of the invention to provide a decompression shaft sterilizer for use with extremely high moisture products which controls the in-feed depth of the product at the inlet while broadening the product bed depth at the outlet.

It is still another object of the invention that the decompression area slow the product speed and allow more exposure and time for exposure to the microwaves, thus improving the efficiency of sterilization.

In accomplishing these and other objects, there has been provided, in accordance with one aspect of the present invention, a microwave applicator having an inner and outer chamber. The inner chamber receives microwaves which disperse from a longitudinal axis from a single source and are diverted out of the first chamber by diverters. The diverters interrupt the microwave flow and direct it through holes in the walls of the first chamber into the second chamber. In the second chamber, product travelling from the inlet to the outlet is radiated with the microwave radiation diverted through the holes. Microwaves which are not absorbed by the product are reflected by the interior wall of the outer chamber and the exterior wall of the inner chamber which are reflective to microwaves. The interior wall of the outer chamber may also have a spiral shape to increase its microwave reflectivity characteristics. Liquid material can pass through the outer chamber without any additional assistance. Solids or solid-line materials can be moved through the outer chamber using a screw type or helix configuration unit. The pitch of the helix can be varied, preferably in segments, to accommodate the moisture content of the materials. The variation of the pitch along the length can slow the product down to increase the holding time in the core and, hence, increase the efficiency of the microwave exposure. In addition, the shaft of the conveyor can be varied from a straight shaft, which permits maximum loading of the unit with the variation of the heating controlled only by the speed of the helix, to a compressive unit in which the product bed depth is decreased at the discharge end for use with highly infectious low moisture content materials.

A decompressive microwave heating unit can be used for extremely high moisture products which cannot be pumped, or slurred and then pumped, through the sterilizer unit. In the decompressive microwave heating unit, the product bed depth at the outlet is allowed to increase while the in-feed depth of the product at the inlet is controlled to avoid overloading the microwave distribution in the feed. As a result of the decompression, the product speed slows and more of the material is exposed to microwaves for a longer time period to effect better heating or sterilization.

According to another aspect of the present invention, a method for heating material has been provided that comprises the steps of applying electromagnetic radiation from a single source into a first chamber; diverting at least a portion of the electromagnetic radiation from the first chamber into a second chamber provided around said first chamber; and then transporting material through the second chamber such that the material is heated by absorption of electromagnetic radiation.

BRIEF DESCRIPTION OF THE DRAWINGS

The above and other objects of the invention will be described by reference to the drawings in which:

FIG. 1 is a side view of a high density liquid heating unit showing the route of microwave travel;

FIG. 2 is a side view of a heating unit with a straight line shaft sterilizer;

FIG. 3 is a top view of the microwave applicator;

FIG. 6 is a side view of a decompression shaft sterilizer;

FIG. 7 is a side view of a variable pitch screw or helix surrounding the microwave applicator;

FIG. 12 illustrates a spiral pattern of holes to provide a spiral pattern of energy wave diverters.

DETAILED DESCRIPTION OF PREFERRED EMBODIMENTS

Figure 4:
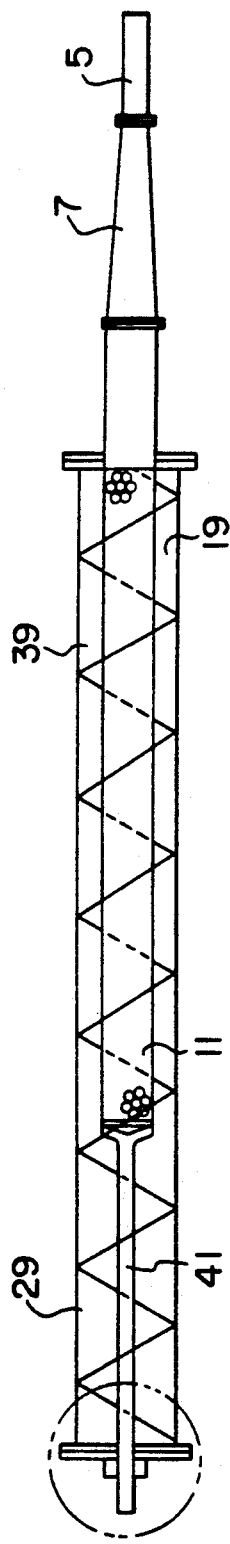
FIG. 4 illustrates a slotted hole punch pattern.

An in-line electromagnetic energy applicator according to the present invention has an electromagnetic energy generation unit for transmitting energy waves along a longitudinal axis. The energy waves, preferably of microwave wavelength, are transmitted into a first chamber with a plurality of openings in its walls. A second chamber surrounds the first chamber at some distance. The first chamber has at least one electromagnetic energy diverter which intersects waves in the first chamber as they disperse from a longitudinal axis or are reflected off reflective material on the inner walls of the first chamber. This causes the electromagnetic energy to be diverted through the openings into the second chamber. The second chamber has a product inlet and outlet and may also be equipped with a conveyor for moving product from the inlet to the outlet. Electromagnetic energy entering through the holes is absorbed by the product in the second chamber as it passes from the inlet to the outlet resulting in heating of the product. The inner walls of the second chamber and the outer walls of the first chamber are made reflective to divert energy not absorbed by the product back toward the product to improve heating efficiency. Absorption of the electromagnetic energy by the product both directly as the waves pass through the holes and indirectly as the waves are reflected within the second chamber allows highly efficient heating of the product. In addition, heating of the product to very high temperatures for sterilization of highly contaminated wastes is possible due to efficiencies achieved from the use of direct and reflected energy.

FIG. 1 shows one configuration of a heating unit using an in-line applicator. The heating unit shown generally at 1 has an electromagnetic energy wave applicator 3 which has an electromagnetic energy wave generation unit 5. Electromagnetic waves 7 are transmitted through transition section 9 to inner chamber 11. Inner chamber 11 has a surrounding wall 13 with a plurality of holes 15 Walls 13 are surrounded by a second set of walls 17 which, with walls 13 form a second or outer chamber 19.

Outer chamber 19 also has product inlet 21 on the side nearest the electromagnetic energy wave generator and an outlet 23 on an opposite end. In order to divert microwaves 7 from inner chamber 11 to outer chamber 19, a plurality of diverters 25 are located along an interior portion of walls 13 of inner chamber. As shown in FIG. 1, the diverters are formed as a series of inverted reducing cones 25 facing the microwave length. The angle of the cones 25 increases relative to angle of the wavelength compared to the directional flow of microwaves from the electromagnetic energy wave generation unit 5. This is done to concentrate the deflection of the microwaves through the holes into the product to be heated in the outer chamber. It also causes the wavelength to hit the interior wall of the outer chamber at different angles, which results in more radical bounce to create a crisscross microwave pattern for better exposure of the product. A small cone 27 at the end of the inner chamber deflects any wavelengths that have not been affected by the preceding microwave diverters.

As the microwaves in the inner chamber are interrupted and diverted by cone diverters 25 and 27, they are transmitted through holes 15 into outer chamber 19. Product passing from inlet 21 to outlet 23 through outer chamber 19 is radiated by the microwaves passing through the holes. Microwaves which are not absorbed by the product are reflected off the inner surface of the outer chamber to be absorbed by the product on a reflected path. Microwaves which are not absorbed at this stage are again reflected off the outside walls 15 of inner chamber 13. As a result, material passing through the outer chamber is efficiently radiated and heated. In order to prevent product in the outer chamber 19 from falling into the inner chamber 13, the holes can be sealed with an external sleeve 16 made from material which is substantially transparent to microwaves. One such material is TELFON. Alternatively, the entire outer wall 15 of inner chamber 13 can be surrounded by the sleeve. For example, the inner tube applicator assembly can be inserted directly into the cavity inside the sleeve. In addition, a screw type conveyor which is inside the outer chamber, as discussed below, can incorporate the sleeve into which the applicator is inserted.

The length of the outer chamber is longer than the length of the inner chamber. As is further discussed below, this allows further application of microwaves to product in the distal section 29 of the heating unit furthest from the electromagnetic energy wave generating unit 5.

FIG. 2 shows a top view of the microwave applicator which is formed by microwave energy generating unit 5, transition coupling 7 and inner chamber 11. The electromagnetic waves typically have wave lengths of between 0.3 cm and 30 cm, corresponding to frequencies of 1 GHz to 100 GHz. For sterilizing infectious wastes, the generator could be constructed to generate 80,000 Watts of usable output energy. However, other amounts of power could be used for other applications.

Figure 8:
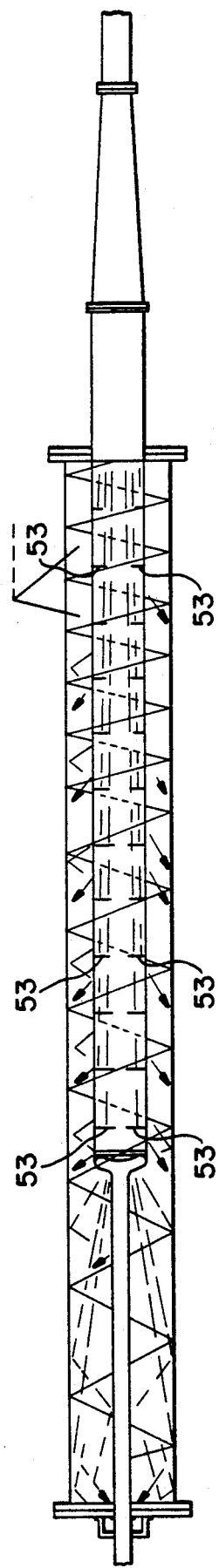
FIG. 8 is a side view of a straight shaft sterilizer with a variable screw.

As shown in FIG. 2, a portion of inner chamber 11 has holes 15 which are formed in lines substantially parallel to each other with adjacent lines of holes being offset. FIG. 3 further illustrates the orientation of the holes 15 and their shape. In a preferred embodiment, each hole 15 has a substantially continuous or curved end 31 and a substantially discontinuous or squared end 33. The curved ends of the holes are on the side closest to the electromagnetic energy wave generating unit 5. As shown in FIGS. 8 and 10, protrusions 53 can be extended from holes 15 into the interior portion of the inner chamber to form microwave diverters. Protrusions 53 are used instead of cones 25 in applications which require very even heating of the material in the chamber with a minimum of hot spots. Cones 25 and 27 are best used as energy diverters when the material to be heated has a high moisture level and can tolerate hot and cold spots. High moisture content may result from the material itself or may be the result of pre-treatments, such as steam heating of the material to pass through the applicator.

The extension of the protrusions 53 into the inner chamber 11 becomes increasingly larger as the distance from electromagnetic energy wave generating unit 5 increases. The protrusions 53 can be individual pieces connected to the inner chamber walls. Preferably, however, the protrusions 53 are formed by punching the holes into the walls of the inner chamber and using the punched lip to form the protrusion. Each punched hole in the line would have an increased size protrusion or lip 53 protruding into the flow of the wavelength, so as to direct the wavelength out of the slot at each contact with the punched lip. The wavelength is then directed into the product in the outer chamber, and, if not absorbed, hits the side wall of the outer chamber and then bounces back toward the product. With multiple waves, this procedure sets up a crossing of wavelengths bouncing against the chamber wall and the applicator metal, thus increasing the exposure to the material to be sterilized.

Hole size is a function of energy required for the heating application, such as sterilization. For instance, if an electromagnetic energy wave-generating unit is used with a large power capability on the order of 100,000M Watts, and the material to be sterilized has a solid-to-liquid ratio between 12% and 15% and if a conveyor moves the material through the outer tube at 250 lbs/hr, then the holes are sized to be ¾ inch by 1¼ inch. For applications in which the flow rate or the solid-to liquid-ratio is different, the required size of each hole changes proportionally, according to a linear relationship. For example, an applicator with a 50,000M Watt power source and hole sizes whose area is 50% that above for the 100,000M Watt power source would accommodate loads of 125 lbs/hr.

As another example of the linear relationship assume that an applicator has a length required for a 100,000M Watt power source. The applicator typically can accommodate turn down of 60% power without producing either hot spots or areas of low heat transfer in the material to be heated. Operating such an applicator at less than 60% of the power, for example, to accommodate lower temperatures, results in cold spots (low heat transfer areas) generally located in the material to be heated near the middle of the applicator. This is because a large portion of the energy escapes in the first section of the applicator nearest the power source. As a result a wavelength bouncing pattern is not established and much of the heating effect achieved from bouncing electromagnetic waves is lost. Some waves are reflected off the end opposite the power source, so that the least heating tends to be in the middle of the applicator. By reducing the power capability to 60% or 60,000 MW and similarly reducing the size of the applicator and its elements by the same percentage to 60% of the size used with a 100,000M Watt source, a wavelength bouncing pattern can again be established. Thus, the length of the inner and outer chambers and the size of the holes and protrusions are arranged to be 60% of the size required for the 100,000MW power source. It should be noted that the distance from the inner chamber 11 to the walls 17 of the outer chamber 19 is not changed to accommodate the same wavelength. This is to insure reflective bounce for better heating. Since effective operation can be maintained to a turndown of power to 60% of the source capability, such a configuration would operate at power levels between 36,000M Watts and 60,000M Watts.

In heating applications requiring especially even heating, better distribution of the microwaves can be obtained by arranging the protrusions according to a spiral pattern. The spiral pattern is arranged to be clockwise or counter clockwise to correspond to the spiral pattern of screw type product conveyors which move the material to be heated through the outer chamber as discussed below. Such a spiral pattern of protrusions can be established by offsetting the centerlines in a horizontal plane of each row of holes by five to ten degrees from the centerline of the adjacent row as illustrated in FIG. 12. Eventually, the centerline of a row matches the centerline of a first row. The spiral pattern of protrusions along with the increasing size of each protrusion as the distance from the electromagnetic wave generator increases work together with the spiral screw shaped conveyors to establish greater distribution of electromagnetic energy to the product passing through the outer chamber.

In applicators employing cones rather than protrusions, hole size is reduced as described above. The size of the center cone 27 decreases in the same proportion as described above. It should be noted that the cone type applicator can be employed in a screw type chamber discussed below.

Figure 11:
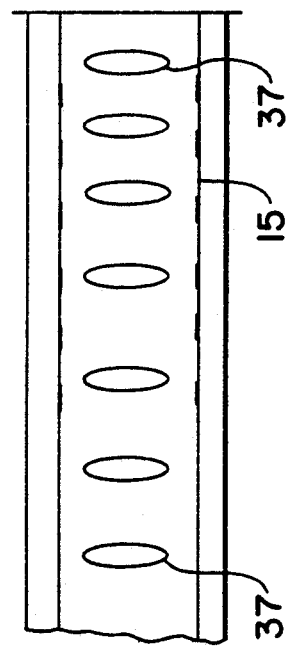
FIG. 11 illustrates a plurality of discs serving as energy wave diverters in the portion of the applicator having a hole pattern.
Figure 10D:
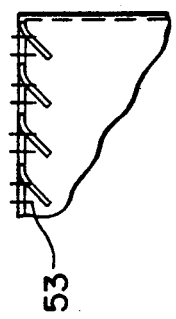
Figure 10C:
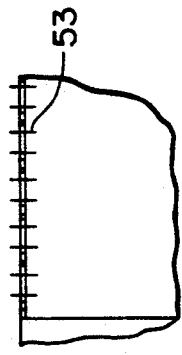
Figure 10B:
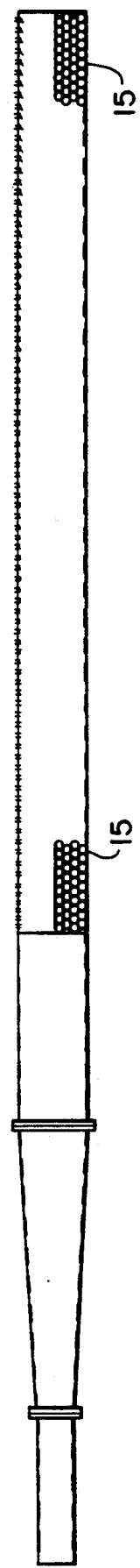

FIG. 11 illustrates another possible microwave diverter. In the microwave diverter arrangement shown in FIG. 11, a plurality of disks 37 is used to interrupt the wave lengths and divert the microwaves out of holes 15. FIG. 12 shows a spiral or screw type diverter pattern of the lips or protrusions in which waves traveling through inner chamber 11 are interrupted by the protruding portions arranged in the screw pattern and are then diverted out holes 15 to the second chamber. It should be noted that the size of the screw protrusions can be varied from one end of the applicator unit to the other and that the spiral or screw type pattern follows the right or left hand screw pattern of the screw type conveyor in the outer chamber.

The heating unit 1, shown in FIG. 1, works well for liquid product which is easily pumped in and removed. Solids and semi-solids require a conveyor means to traverse the outer chamber 19. FIG. 4 shows a single pitch helical or screw type conveyor 39 used in the outer chamber 19. As discussed below, for some applications one or more pitches are used. Screw type conveyors can be constructed of microwave transparent material, such as TEFLON, to avoid affecting the microwave paths in the outer chamber. Extending from the end of first chamber 11 to the end of second chamber 19 in the area 29 of the second chamber is straight shaft 41. The straight shaft full pitch unit allows sufficient heating of products with a substantially consistent moisture mix. The straight shaft permits maximum loading of the unit so that the variations in heating are controlled only by the speed at which helical coil 39 is turned.

Figure 5:
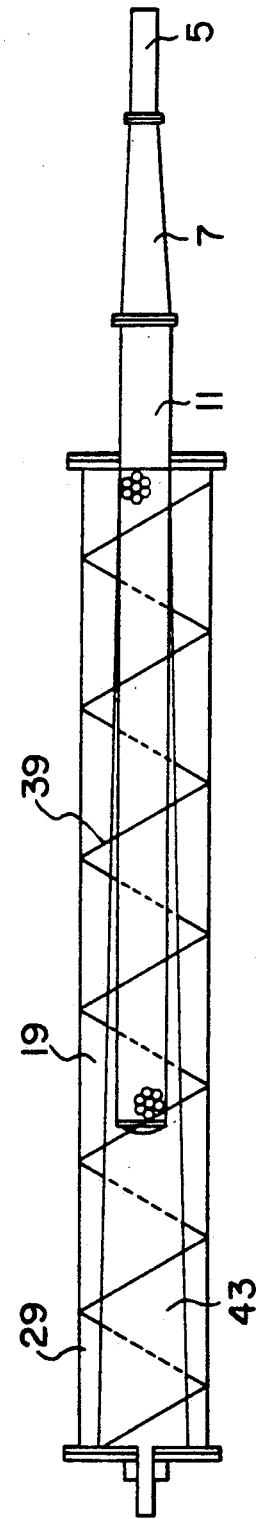
FIG. 5 is a side view of a compression shaft sterilizer.

FIG. 5 illustrates a compression shaft heating unit with a full pitch helical coil for conveying the materials. In the compressive shaft, the product bed depth at the discharge end is forced to be narrower than the product bed depth at the in-feed end. This is because of the increasing thickness of shaft 43 in the outer chamber 19. As FIG. 5 shows, the distance between the walls of inner chamber 11 and outer chamber 19 is greatest at the in-feed end nearest the electromagnetic energy wave generation unit 5 and narrowest at the end of the outer tube furthest from the electromagnetic energy wave generation unit 5. As a result, the bed depth of the product is greater at the in-feed end than at the discharge end. This type of unit would be used for materials with low moisture content and which may be very infectious. The compression end maximizes the exposure to the wave pattern on the discharge end by decreasing the product bed depth. In addition, this configuration allows for a large volumetric feed and maximizes the in-feed rate.

FIG. 6 illustrates a decompression shaft microwave heating unit. In this unit, the distance between the walls of the shaft and the walls of the outer tube is smallest at the infeed end nearest the electromagnetic energy wave generation unit 5 and largest at the discharge end on the opposite side of the outer chamber 19. This controls the in-feed depth of the product at the inlet, so as not to overload the microwave distribution in the feed. As the product traverses the length of the outer tube, the decompression slows the product speed and allows more of the material to be exposed for a greater time period to the microwaves. This provides better heating and would therefore be best used for extremely high moisture content products which cannot be pumped or which could not be slurred and then pumped through a liquid unit such as that shown in FIG. 1.

FIG. 7 illustrates a variable pitch helical conveyor. One example is shown in FIG. 7, in which the helical conveyor 39 has a full pitch section 47, a ¾ pitch section 49 and a ½ pitch section 51. These sections or segments in the pitch of the conveyor allow for variations in the product flow through the outer chamber. As shown in FIG. 7, in the half pitch section 51 the number of turns is twice that of the full pitch section 47. As product moves from the half pitch segment toward the full pitch segment of the helical conveyor coil, it slows down and the holding time in the second chamber during which the product is irradiated with electromagnetic energy waves is increased. As a result, the heating and sterilization efficiency of the product is improved. In some cases, this may also allow operating at lower power levels.

FIG. 8 illustrates a straight shaft sterilizer with a variable pitch helix or screw. As FIGS. 4, 5 and 6 also illustrate, any of these configurations can be used with a variable pitch screw to achieve the effects discussed above. Thus, it will be known to those of ordinary skill that the full pitch versions shown in FIGS. 4, 5 and 6 are by way of illustration and not by limitation.

Figure 9:
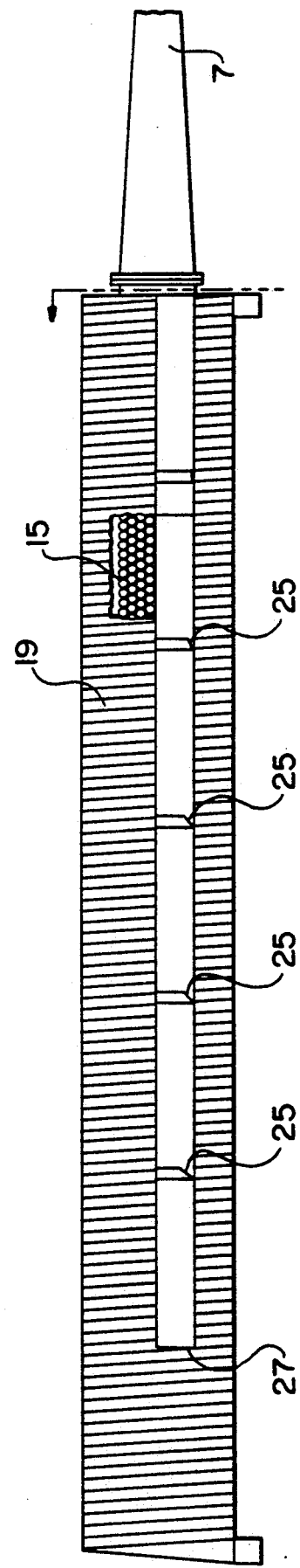
FIG. 9 is a side view of a heating unit employing a screw pattern on the inside of the outer tube.
Figure 10A:
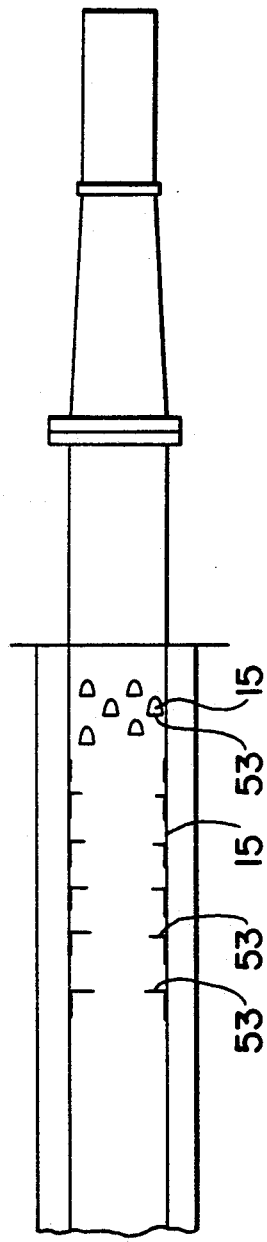
FIGS. 10a and 10b illustrate a hole pattern having progressively increasing size protrusions.

FIG. 9 further illustrates the use of cones in the inner chamber to divert microwaves into the outer chamber. FIG. 9 also shows outer chamber 19 having interior walls with a substantially spiral shape. This spiral rib along the interior walls of chamber 19 causes a deflection in the directional flow of microwaves, thus increasing the exposure pattern. As a result the efficiency of microwave energy transfer to the product within the outer chamber is increased and more effective heating is accomplished.

While specific embodiments of the invention have been described and illustrated, it will be clear that variations in the details of the embodiments specifically illustrated and described may be made without departing from the true spirit and scope of the invention as defined in the appended claims.

What is claimed is:

1. An apparatus for applying microwave energy to a product, comprising:
    an electromagnetic energy generation unit for transmitting electromagnetic energy waves which disperse from a longitudinal axis from an entrance of the electromagnetic energy waves;
    a first chamber with first interconnected walls forming an enclosure having an interior for receiving the electromagnetic energy waves and an exterior, the walls having a plurality of openings;
    a second chamber formed by second interconnected walls surrounding the first chamber at a distance from the exterior of first chamber, the second chamber having a product inlet for receiving product and a product outlet for removing product passing through the second chamber from the product inlet to the product outlet; and
    at least one electromagnetic energy diverter within the interior of the first chamber for diverting at least some of the electromagnetic energy waves dispersing from the longitudinal axis into the openings to irradiate product passing through the second chamber.

2. The apparatus recited in claim 1, wherein the electromagnetic energy diverters comprise projections extending from the openings into the interior of the first chamber.

3. The apparatus recited in claim 2, wherein the projections comprise portions of the walls remaining after holes are punched into the walls.

4. The apparatus recited in claim 2, wherein the projections vary in size.

5. The apparatus recited in claim 4, wherein the projections vary in size from a smallest projection at a hole nearest the energy generation unit on a longitudinal axis to a largest projection at a hole furthest from the energy generation unit on a longitudinal axis.

6. The apparatus recited in claim 5, wherein the projections are increasingly larger from the smallest to largest projection.

7. The apparatus recited in claim 1, wherein the energy diverters comprise at least one disk located in the first chamber to intersect the electromagnetic energy waves.

8. The apparatus recited in claim 7, wherein the disks are of variable size.

9. The apparatus recited in claim 1, wherein the energy diverter in the first chamber comprises a generally spiral shaped unit having a centerline along the longitudinal axis, with projecting portions of the spiral extending outward from the centerline to the interior of the first chamber.

10. The apparatus recited in claim 1, wherein the openings comprise elongated holes.

11. The apparatus recited in claim 10, wherein at least some of the elongated holes have a first end with a generally curved shape and a second end with a generally straight shape.

12. The apparatus recited in claim 11, wherein the first ends are located on a side nearest the energy generation unit and the second ends are generally square and located opposite the first end.

13. The apparatus recited in claim 1, wherein the openings further comprise first and second pluralities of openings, the first and second pluralities of openings being generally parallel and offset in a longitudinal direction.

14. The apparatus recited in claim 1, wherein the second chamber is longer in a longitudinal direction than the first chamber.

15. The apparatus recited in claim 1, wherein the energy diverters in the first chamber comprise a series of interrupting cones along the interior of the first chamber.

16. The apparatus recited in claim 15, wherein the energy interrupting cones are placed at angles to the electromagnetic energy waves dispersing from the longitudinal axis.

17. The apparatus recited in claim 16, wherein the angle of the interrupting cones progressively increases from a smallest angle at a cone nearest the electromagnetic energy generation unit to a largest angle at a cone farthest from the electromagnetic energy generation unit.

18. The apparatus recited in claim 1, further comprising an energy interrupting cone, at an end opposite the energy generation unit, for deflecting electromagnetic energy waves not deflected by other diverters.

19. The apparatus recited in claim 1, wherein the second walls surrounding the first chamber have an energy reflective interior side.

20. The apparatus recited in claim 1, wherein the interior sides of the second walls have a generally spiral rib.

21. The apparatus recited in claim 1, further comprising a conveyor in the second chamber for transporting products from the product inlet to the product outlet.

22. The apparatus recited in claim 21, wherein the conveyor is a generally spiral shaped screw type conveyor.

23. The apparatus recited in claim 22, wherein the spiral shaped screw has a substantially uniform pitch such that a longitudinal distance between projecting portions of the screw is uniform.

24. The apparatus recited in claim 22, wherein the spiral shaped screw has a variable pitch such that a longitudinal distance between projecting portions of the screw is variable.

25. The apparatus recited in claim 24, wherein the screw type conveyor comprises at least two segments having different pitch, with each segment having uniform pitch within the segment.

26. The apparatus recited in claim 25, wherein a segment farthest from the energy generation unit is a full pitch segment having a longest longitudinal distance between projecting portions of the screw, and wherein segments closer to the energy generating unit have smaller longitudinal distances between projecting portions of the screw.

27. The apparatus recite in claim 21, wherein the second chamber is longer in longitudinal direction than the first chamber.

28. The apparatus recited in claim 27, further comprising a shaft extending along the longitudinal axis into the second chamber from exterior sides of the first chamber.

29. The apparatus recited in claim 28, wherein the shaft extends from an end of the first chamber opposite the energy generation unit and has a substantially uniform thickness.

30. The apparatus recited in claim 28, wherein the shaft has an increasing thickness throughout the second chamber from an end nearest the electromagnetic energy generation unit to an opposite end.

31. The apparatus recited in claim 28, wherein the shaft has a decreasing thickness throughout the second chamber from an end nearest the electromagnetic energy generation unit to an opposite end.

32. The apparatus recited in claim 1, wherein the distance from the exterior of the first chamber to the walls of the second chamber is selected to optimize heating of the product resulting from transmitting electromagnetic energy waves of a preselected wavelength.

33. The apparatus recited in claim 1, further comprising microwave transparent sleeving surrounding the holes.

34. An apparatus for applying microwave energy to a product comprising:
an inner chamber and a surrounding chamber separated at a distance from the inner chamber, the inner chamber having sides with a first plurality of holes, each hole having a projection extending towards an interior of the chamber, the outer chamber having a product inlet and a product outlet and a conveyor from conveying product from the inlet toward the outlet;
a microwave energy generation unit for transmitting microwave energy into an interior of the inner chamber, the microwave energy being diverted by the projections through the holes toward the outer chamber for radiating product in the outer chamber.

35. The apparatus recited in claim 32, further comprising microwave transparent sleeving surrounding the holes.

36. The apparatus recited in claim 1, wherein the electromagnetic energy diverters comprise projections extending from the opening in the first chamber, the projections being arranged in a spiral pattern.

37. The apparatus recited in claim 36 wherein the spiral pattern is formed in a same direction as a direction of a screw type conveyor in the second chamber.

38. A method of applying microwave energy to a product, the method comprising the steps of:
transmitting electromagnetic energy waves from an electromagnetic energy generation unit along a longitudinal axis from an entrance of the electromagnetic energy waves so as to disperse the electromagnetic energy waves from the longitudinal axis;
receiving the electromagnetic energy waves into an interior of a first chamber with first interconnected walls forming an enclosure having an interior and an exterior, the walls having a plurality of openings;
passing a product from a product inlet to a product outlet of a second chamber formed by second interconnected walls surrounding the first chamber at a distance from the exterior of first chamber, the inlet receiving the product and the outlet removing the product passed through the second chamber; and
with at least one electromagnetic energy diverter within the interior of the first chamber, diverting at least some of the electromagnetic energy waves dispersing from the longitudinal axis into the openings to irradiate the product passing through the second chamber.

39. The method recited in claim 38, wherein the step of diverting at least some of the electromagnetic energy waves comprises diverting electromagnetic energy with projections extending from the openings into the interior of the first chamber.

40. The method recited in claim 39, wherein the energy is diverted with projections comprised of portions of the walls remaining after holes are punched into the walls.

41. The method recited in claim 39, wherein the electromagnetic energy waves are diverted by projections that vary in size.

42. The method recited in claim 39, wherein the electromagnetic energy waves are diverted by projections varying in size from a smallest projection at a hole nearest the energy generation unit on a longitudinal axis to a largest projection at a hole furthest from the energy generation unit on a longitudinal axis.

43. The method recited in claim 42, wherein the electromagnetic energy waves are diverted by projections increasingly larger from the smaller to largest projection.

44. The method recited in claim 38, wherein the electromagnetic energy waves are diverted by diverters comprising at least one disk located in the first chamber to intersect the dispersing electromagnetic energy waves.

45. The method recited in claim 44, wherein the electromagnetic energy waves are diverted by disks of variable size.

46. The method recited in claim 38, wherein the electromagnetic energy waves are diverted in the first chamber by a diverter comprising a generally spiral shaped unit having a centerline along the longitudinal axis, with projecting portions of the spiral extending outward from the centerline to the interior of the first chamber.

47. The method recited in claim 38, wherein the energy is diverted through openings comprised of elongated holes.

48. The method recited in claim 47, wherein at least some of the elongated holes are formed having a first end with a generally curved shape and a second end with a generally straight shape.

49. The method recited in claim 48, wherein the first ends are located on a side nearest the energy generation unit and the second ends are generally square and located opposite the first end.

50. The method recited in claim 38, wherein the electromagnetic energy waves are diverted through openings comprising first and second pluralities of openings, the first and second pluralities of openings being generally parallel and offset in a longitudinal direction.

51. The method recited in claim 38, wherein the second chamber is longer in a longitudinal direction than the first chamber.

52. The method recited in claim 38, wherein the electromagnetic energy waves are diverted by diverters in the first chamber comprising a series of interrupting cones along the interior of the first chamber.

53. The method recited in claim 52, wherein the energy interrupting cones are placed at angles to the electromagnetic energy waves dispersing from the longitudinal axis.

54. The method recited in claim 53, wherein the angle of the interrupting cones progressively increases from a smallest angle at a cone nearest the electromagnetic energy generation unit to a largest angle at a cone farthest from the electromagnetic energy generation unit.

55. The method recited in claim 38, further comprising deflecting electromagnetic energy waves not deflected by other diverters with an energy interrupting cone at an end opposite the energy generation unit.

56. The method recited in claim 38, wherein the second walls surrounding the first chamber reflect energy with an energy reflective interior side.

57. The method recited in claim 38, wherein the interior sides of the second walls have a generally spiral rib.

58. The method recited in claim 38, further comprising transporting products from the product inlet to the product outlet by a conveyor in the second chamber.

59. The method recited in claim 58, wherein the conveyor is a generally spiral shaped screw type conveyor.

60. The method recited in claim 59, wherein the spiral shaped screw has a substantially uniform pitch such that a longitudinal distance between projecting portions of the screw is uniform.

61. The method recited in claim 59, wherein the spiral shaped screw has a variable pitch such that a longitudinal distance between projecting portions of the screw is variable.

62. The method recited in claim 61, wherein the screw type conveyor comprises at least two segments having different pitch, with each segment having uniform pitch within the segment.

63. The method recited in claim 62, wherein a segment farthest from the energy generation unit is a full pitch segment having a longest longitudinal distance between projecting portions of the screw, and wherein segments closer to the energy generating unit have smaller longitudinal distances between projecting portions of the screw.

64. The method recited in claim 58, wherein the second chamber is longer in longitudinal direction than the first chamber.

65. The method recited in claim 64, wherein a shaft is extended along the longitudinal axis into the second chamber from exterior sides of the first chamber.

66. The method recited in claim 65, wherein the shaft extends from an end of the first chamber opposite the energy generation unit and has a substantially uniform thickness.

67. The method recited in claim 65, wherein the shaft has an increasing thickness throughout the second chamber from an end nearest the electromagnetic energy generation unit to an opposite end.

68. The method recited in claim 65, wherein the shaft has a decreasing thickness throughout the second chamber from an end nearest the electromagnetic energy generation unit to an opposite end.

69. The method recited in claim 38, wherein the distance from the exterior of the first chamber to the walls of the second chamber is selected to optimize heating of the product resulting from transmitting electromagnetic energy waves of a preselected wavelength.

70. The method recited in claim 38, wherein the holes are surrounded with microwave transparent sleeving.

71. A method of applying microwave energy to a product, the method comprising the steps of:
   surrounding an inner chamber with a surrounding chamber separated at a distance from the inner chamber, the inner chamber having sides with a first plurality of holes, each hole having a projection extending towards an interior of the chamber, the outer chamber having a product inlet and a product outlet and a conveyor from conveying product from the inlet toward the outlet;
   transmitting microwave energy into an interior of the inner chamber, and diverting the microwave energy with the projections through the holes toward the outer chamber thereby radiating product in the outer chamber.

72. The method recited in claim 71, wherein the holes are surrounded by microwave transparent sleeving.

73. The method recited in claim 38, wherein the electromagnetic energy waves are diverted by electromagnetic energy diverters comprising projections extending from the opening in the first chamber, the projections being arranged in a spiral pattern.

74. The method recited in claim 73 wherein the spiral pattern is formed in a same direction as a direction of a screw type conveyor in the second chamber.

* * * * *